(12) United States Patent
Marin et al.

(10) Patent No.: US 10,980,655 B1
(45) Date of Patent: Apr. 20, 2021

(54) DYNAMIC FOOT PLATE

(71) Applicant: MDPO LLC, Sunrise, FL (US)

(72) Inventors: Luis E. Marin, Sunrise, FL (US); Steve Ward, Miami, FL (US)

(73) Assignee: MDPO LLC, Sunrise, FL (US)

( * ) Notice: Subject to any disclaimer, the term of this patent is extended or adjusted under 35 U.S.C. 154(b) by 358 days.

(21) Appl. No.: 15/794,493

(22) Filed: Oct. 26, 2017

Related U.S. Application Data (63) Continuation-in-part of application No. 15/167,158, filed on May 27, 2016, which is a continuation-in-part of application No. 14/716,286, filed on May 19, 2015, now Pat. No. 10,463,522, which is a continuation-in-part of application No. 14/099,177, filed on Dec. 6, 2013, now abandoned.

(60) Provisional application No. 62/168,287, filed on May 29, 2015, provisional application No. 61/782,286, filed on Mar. 14, 2013.

(51) Int. Cl.
*A61B 17/64* (2006.01)
*A61F 5/01* (2006.01)
*A61B 17/62* (2006.01)

(52) U.S. Cl.
CPC ............ *A61F 5/0127* (2013.01); *A61B 17/62* (2013.01); *A61B 17/645* (2013.01); *A61B 17/6416* (2013.01); *A61B 17/6441* (2013.01)

(58) Field of Classification Search
CPC .............................. A61F 5/0111; A61F 5/0127
See application file for complete search history.

(56) References Cited

U.S. PATENT DOCUMENTS

| | | |
|---|---|---|
| 2,020,262 A | 11/1935 | Longfellow |
| 2,035,952 A | 3/1936 | Ettinger |
| 2,079,567 A | 5/1937 | Anderson |
| 2,393,831 A | 1/1946 | Stader |
| 2,406,987 A | 9/1946 | Anderson |
| 3,941,123 A | 3/1976 | Volkov et al. |
| 4,176,627 A | 12/1979 | Bassi |
| 4,308,863 A | 1/1982 | Fischer |
| 4,338,927 A | 7/1982 | Volkov et al. |
| 4,535,763 A | 8/1985 | Jacquet |
| 4,607,625 A | 8/1986 | Schenck |

(Continued)

FOREIGN PATENT DOCUMENTS

| | | |
|---|---|---|
| EP | 2194881 | 11/2016 |
| RU | 2391931 | 6/2010 |

(Continued)

*Primary Examiner* — Nicholas J Plionis
(74) *Attorney, Agent, or Firm* — Malloy & Malloy, P.L.

(57) ABSTRACT

A dynamic foot plate assembly structured for therapeutic use adjacent the ankle area of the body comprising a base element, at least one side element extending along the ankle area, and at least one joint movably and adjustably connecting the base element to the side element for variable displacement of the base element and side element into different operative orientations. The dynamic foot plate assembly may also comprise a plurality of strut members disposed in an interconnecting relationship between either a support member and a side element, or the support member and the base element. The strut members, if present, facilitate the variable relative displacement of the base element, side element and support member into different operative orientations.

23 Claims, 12 Drawing Sheets

(56) References Cited

U.S. PATENT DOCUMENTS

| | | | |
|---|---|---|---|
| 4,624,249 A | 11/1986 | Alvarez Cambras | |
| 4,696,293 A | 9/1987 | Ciullo | |
| 4,768,524 A | 9/1988 | Hardy | |
| 5,062,844 A | 11/1991 | Jamison et al. | |
| 5,067,954 A | 11/1991 | Ilizarov | |
| 5,087,258 A | 2/1992 | Schewior | |
| 5,139,498 A | 8/1992 | Astudillo Ley | |
| 5,358,504 A | 10/1994 | Paley et al. | |
| 5,468,242 A | 11/1995 | Reisberg | |
| 5,496,319 A | 3/1996 | Allard et al. | |
| 5,540,686 A | 7/1996 | Zippel et al. | |
| 5,578,041 A | 11/1996 | Nash et al. | |
| 5,681,309 A | 10/1997 | Ross, Jr. et al. | |
| 5,702,389 A | 12/1997 | Taylor et al. | |
| 5,743,898 A | 4/1998 | Bailey et al. | |
| 5,776,132 A | 7/1998 | Blyakher | |
| 5,788,695 A | 8/1998 | Richardson | |
| 5,814,048 A | 9/1998 | Morgan | |
| 5,891,143 A | 4/1999 | Taylor et al. | |
| 5,931,837 A | 8/1999 | Marsh et al. | |
| 6,030,386 A | 2/2000 | Taylor et al. | |
| 6,328,737 B1 | 12/2001 | Moorcroft et al. | |
| 6,355,037 B1 | 3/2002 | Crosslin et al. | |
| 6,461,358 B1 | 10/2002 | Faccioli et al. | |
| 6,964,663 B2 | 11/2005 | Grant et al. | |
| 7,025,790 B2 | 4/2006 | Parks et al. | |
| 7,048,735 B2 | 5/2006 | Ferrante et al. | |
| 7,189,237 B2 | 3/2007 | Huebner | |
| 7,361,176 B2 | 4/2008 | Cooper et al. | |
| 7,422,593 B2 | 9/2008 | Cresina et al. | |
| 7,806,843 B2 | 10/2010 | Marin | |
| 7,887,498 B2 | 2/2011 | Marin | |
| 8,251,937 B2 | 8/2012 | Marin | |
| 8,439,914 B2 | 5/2013 | Ross et al. | |
| 9,924,968 B2 | 3/2018 | Marin | |
| 10,463,522 B2 | 11/2019 | Marin | |
| 2002/0010465 A1 | 1/2002 | Koo et al. | |
| 2004/0059331 A1 | 3/2004 | Mullaney | |
| 2004/0138659 A1 | 7/2004 | Austin et al. | |
| 2004/0167530 A1 | 8/2004 | Hamel | |
| 2005/0149018 A1 | 7/2005 | Cooper et al. | |
| 2005/0251135 A1 | 11/2005 | Riccione et al. | |
| 2007/0055234 A1 | 3/2007 | McGrath et al. | |
| 2007/0161984 A1* | 7/2007 | Cresina | A61B 17/6425 606/54 |
| 2007/0255280 A1 | 11/2007 | Austin et al. | |
| 2008/0021451 A1 | 1/2008 | Coull et al. | |
| 2009/0082709 A1 | 3/2009 | Marin | |
| 2009/0105621 A1 | 4/2009 | Boyd et al. | |
| 2009/0177197 A1 | 7/2009 | Marin | |
| 2009/0275944 A1* | 11/2009 | Huebner | A61B 17/60 606/54 |
| 2010/0179548 A1 | 7/2010 | Marin | |
| 2010/0234844 A1 | 9/2010 | Edelhauser et al. | |
| 2010/0234896 A1 | 9/2010 | Lorenz et al. | |
| 2010/0312243 A1* | 12/2010 | Ross | A61B 17/62 606/56 |
| 2010/0331840 A1 | 12/2010 | Ross et al. | |
| 2012/0209163 A1 | 8/2012 | Phillips | |
| 2012/0330312 A1 | 12/2012 | Burgherr et al. | |
| 2014/0257287 A1 | 9/2014 | Chang et al. | |
| 2014/0276260 A1 | 9/2014 | Marin | |
| 2015/0032107 A1 | 1/2015 | Marin | |
| 2015/0282973 A1 | 10/2015 | Marin | |

FOREIGN PATENT DOCUMENTS

| | | |
|---|---|---|
| WO | WO 2007/067297 | 6/2007 |
| WO | WO 2007/111576 | 10/2007 |
| WO | WO 2009/042167 | 4/2009 |
| WO | WO 2010/083033 | 7/2010 |
| WO | WO 2014/152559 | 9/2014 |
| WO | WO 2016196498 | 12/2016 |

* cited by examiner

DYNAMIC FOOT PLATE

CLAIM OF PRIORITY

This present application is a continuation-in-part patent application of U.S. patent application having Ser. No. 15/167,158 filed on May 27, 2016, which claims priority under 35 U.S.C. § 119(e) to a provisional patent application having Ser. No. 62/168,287, filing on May 29, 2015. Furthermore, U.S. patent application having Ser. No. 15/167,158 is a continuation-in-part patent application of U.S. patent application having Ser. No. 14/716,286, filed on May 19, 2015, which issued on Nov. 5, 2019 with U.S. Pat. No. 10,463,522 and which is a continuation-in-part patent application of U.S. patent application having Ser. No. 14/099,177, filed on Dec. 6, 2013, which claims priority under 35 U.S.C. § 119(e) to a provisional patent application filed with the U.S. Patent Office on Mar. 14, 2013, and assigned Ser. No. 61/782,286. Each of the above applications is incorporated by reference herein in their entirety.

BACKGROUND OF THE INVENTION

Field of the Invention

This invention is directed to a support assembly for use in operative placement relative to and treatment of the ankle area including the ankle joint, foot and correspondingly disposed lower leg bones. The assembly allows for a variable orientation of at least one of its members, at least one of which is structured for the disposition of at least one transfixion pin for the engagement and treatment of a patient's ankle area.

Description of the Related Art

In the medical treatment of pathologies including, but not limited to, injuries, fractures, etc. to the bone and joints, external fixator assemblies are commonly used to maintain segments of the bone in an intended and/or required stabilized orientation. By way of example, fixator assemblies of the type described may be utilized to treat the fusion of bone tissue as well soft tissue injuries, and situations involving a union of bones which otherwise are difficult to heal. As such, known or conventional fixator assemblies vary in structure, dimension and configuration and are correspondingly adapted to be used with various portions of the body to which they are attached.

Typical fixator structures include at least one connecting bar or rod as well a plurality of clamps for adjustably securing fixation pins, wires, etc. to the bone portions being affected. Further, transfixion pins or wires of the types commonly utilized may extend completely through the bony tissue or may be anchored therein, such as when the long bones of the leg are involved directly or indirectly with the treatment or healing procedure. Further, the term "transfixion member" is generally recognized in the medical field as including the describing of elongated fixation pins which extend completely or at least partially through the bony tissue involved. In contrast, smaller, thicker "half pins" may be utilized in substantially the same manner to stabilize affected tissue but being of a length insufficient to extend completely through the affected bone, joint, etc. This term may also be used in a more generic sense in referring to stabilizing devices, other than pins, such as wires, reduction wires, screws, clamps, etc.

In addition, known external fixator assemblies of the type described may also include support rings which encircle a corresponding body member, wherein such rings or like support elements serve as a supportive base to facilitate proper location of the aforementioned transfixion members. Accordingly, it is commonly understood in the medical profession that fixator assemblies are used to maintain proper orientation of one or more bones or bone segments relative to one another to facilitate healing or alignment.

However, the proper stabilization of tissue typically associated with the joint areas of a patient's body such as, but not limited to, the ankle joint as well as the wrist and other smaller bones associated with the hand involves additional considerations.

It would therefore be beneficial to implement a technology that incorporates dynamic aspects to allow for the acute and/or gradual relocation of a foot, ankle or leg deformity. With the dynamic properties of the assembly, a foot, ankle or leg soft tissue and bony pathology can be corrected. In addition, the calibration of the movable components of the assembly allows for ease of use and increased accuracy of adjustments, allowing the surgeon to correct complicated deformities.

SUMMARY OF THE INVENTION

This invention is directed to a dynamic foot plate assembly primarily, but not exclusively, structured for placement adjacent an ankle area of the body. As referred to herein, the term "ankle area" is intended to describe the ankle joint, as well as bones and associated tissue of the foot and lower portions of the leg including the fibula and tibia. Further, in properly describing the intended position and orientation of the various preferred embodiments of the external fixator assembly of the present invention, terminology including "length of the ankle area" and/or "height of the ankle area" may be utilized synonymously. These terms are meant to refer to the general distance between the bottom of the foot and an area of the lower part of the leg above the ankle joint. Further the ankle area, as used herein, is meant to be descriptive of the bones and other tissue associated with the foot, ankle joint and lower leg which serve to facilitate the functioning of the ankle joint and intended, relative movements of the corresponding foot and leg connected to the ankle joint.

Accordingly, the dynamic foot plate assembly includes a configuration of side elements and joints connected to a base element intended to be disposed adjacent to the ankle area. The side elements are structured to support at least one transfixion pin or like transfixion member in operative engagement with the bones or other associated tissue of the ankle area. Consequently, the dynamic foot plate assembly includes at least one base segment preferably, but not necessarily, having a curvilinear configuration substantially in the form of an arc and/or semi-circle operatively disposed at the medial and lateral longitudinal segments.

In addition, the assembly includes a configuration of joints and side elements attached to the base element and extending transversely from the base element and adjacent the ankle area. The joints and side elements are movably connected and structured to allow variable disposition of the side elements relative to the base element, including but not limited to rotation, raising/lowering, hinging/tilting, and varying the longitudinal spacing/telescoping of the configuration. Some joints may be further capable of being locked or fixed, allowing for the configuration of joints and side elements to become fixed relative to one another. Joints can subsequently be unlocked, restoring the ability for the configuration to once again be articulated.

Further, at least one strut member, which may work in concert with at least one joint, extends from a support member, disposed adjacent the ankle and above the base element, and can be connected to either a base element or a side element to allow for the relative disposition of the dynamic foot plate array into a desired orientation for treatment.

One embodiment of the invention comprises a base element as previously described movably interconnected to two joints, each disposed on an opposing side of the ankle, which are in turn movably interconnected to a pair of side elements extending outwardly from the base along opposing sides of the ankle. One or more strut members are structured to movably interconnect the base element to a support member disposed in spaced relation "above" the base and adjacent to and at least partially surrounding relation to the ankle area. One or more strut members are disposed and structured to movably interconnect the support member to the aforementioned side elements. Accordingly, the plurality of strut members and the at least two joints are structured to cooperatively dispose the base element, side elements and support member into any one of a possible plurality of buried orientations for treatment of the ankle and related areas of the lower leg.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 6:
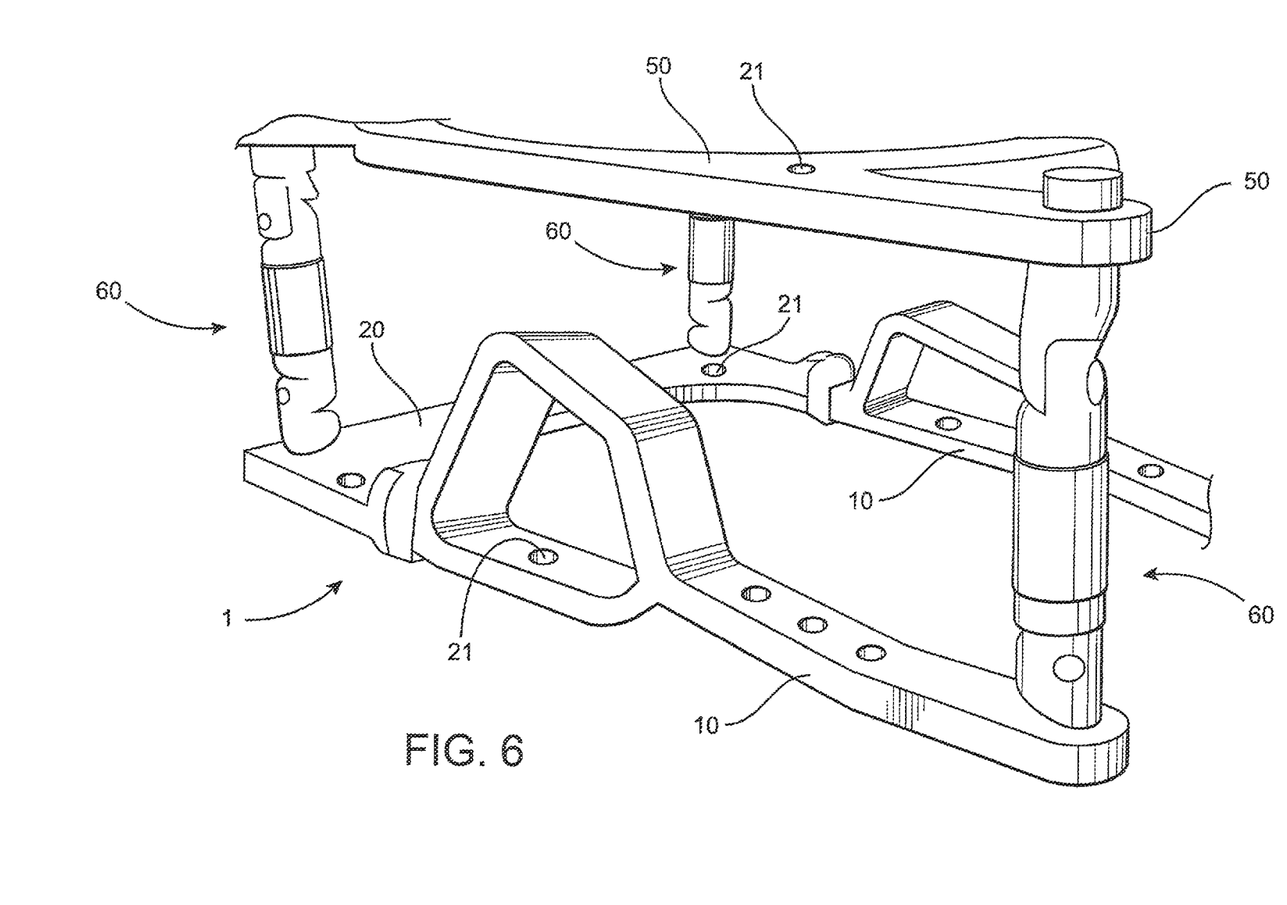
FIG. 6 is a side view in partial cutaway of a plurality of strut members of the preferred embodiment of FIG. 1.
Figure 9:
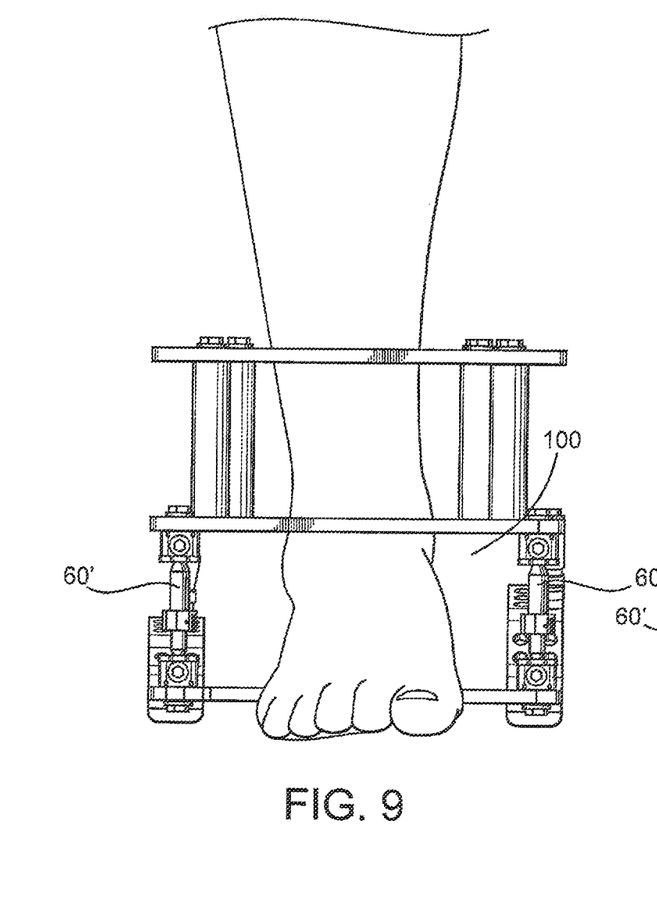
FIG. 9 is a front view of another embodiment of the present invention when operatively positioned relative to an ankle area of a patient.
Figure 10:
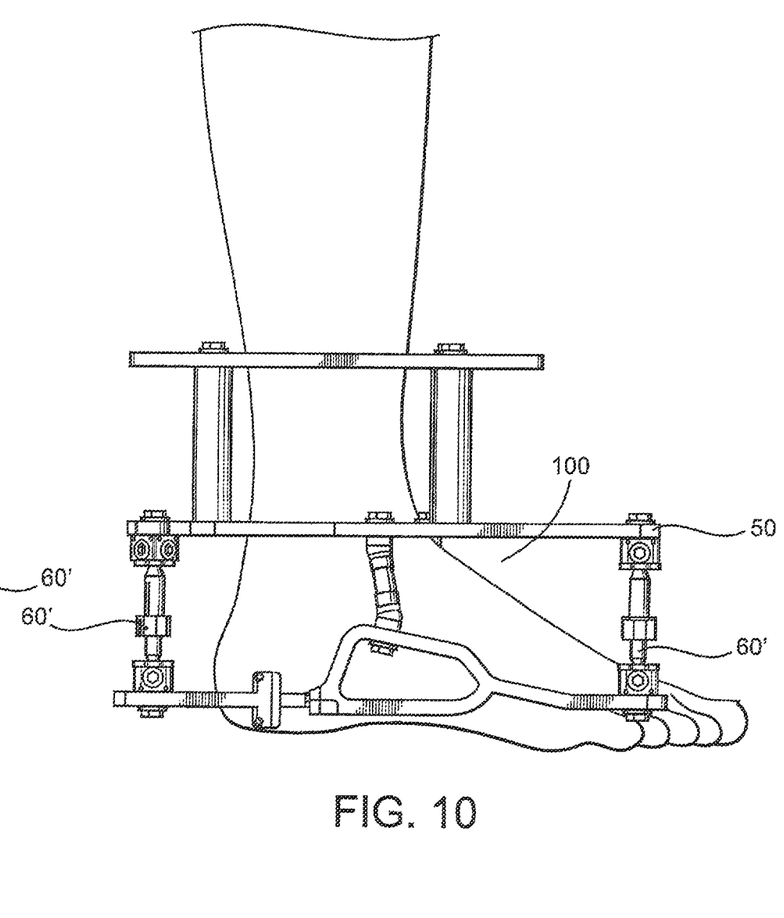
FIG. 10 is a side view of the embodiment of FIG. 9 when operatively positioned relative to an ankle area of a patient.

As represented in the accompanying figures, the present invention is directed to a dynamic foot plate assembly generally indicated as 1 throughout the figures and in particular FIG. 6. As demonstrated, the dynamic foot plate assembly 1 is structured to be operatively positioned and used in a location substantially adjacent the ankle area 100 of a patent as indicated in FIGS. 9 and 10. As set forth above, the ankle area 100 is meant to be descriptive of substantially the entire area, which includes the ankle joint, foot, corresponding portions of the leg bones, including the fibula and tibia, as well as the associated components and tissue. In addition, the terms "height" and "length" of the ankle area 100 are used synonymously herein and refer to the distance from substantially the bottom of the foot, as at, to at least a portion of the long bones of the leg, as at 100.

Figure 11:
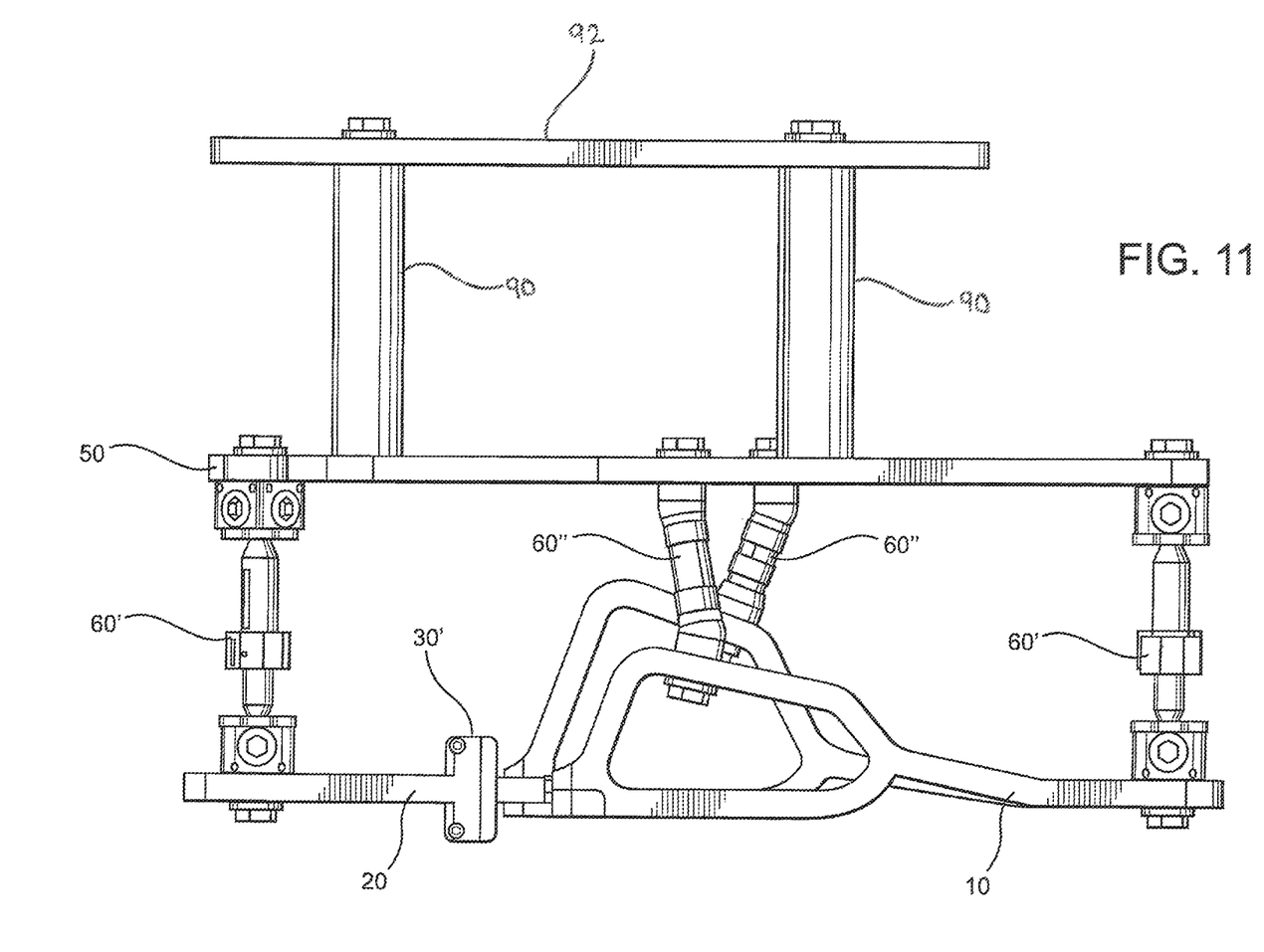
FIG. 11 is a side view of the embodiment of FIG. 9.
Figure 13:
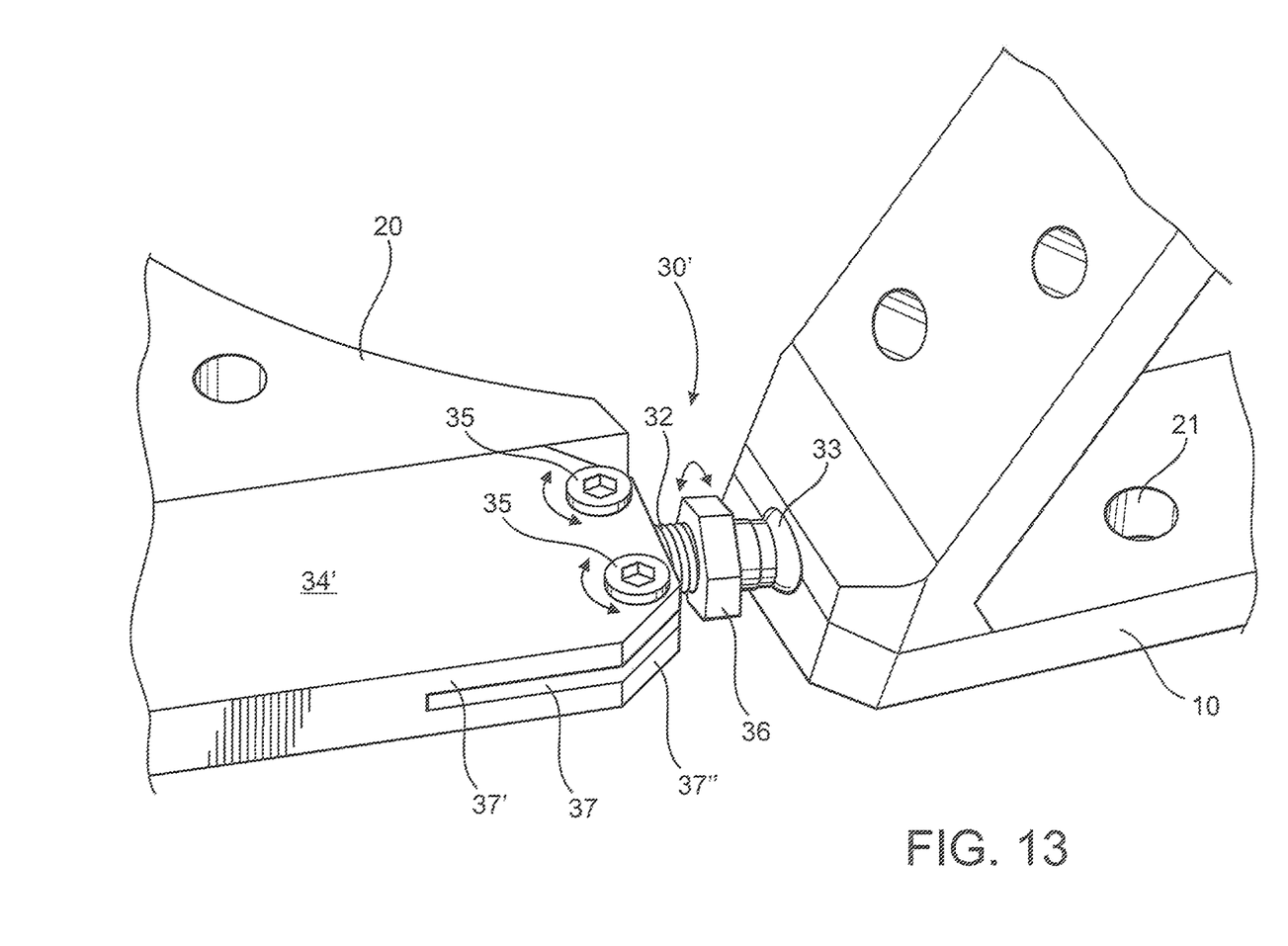
FIG. 13 is a view in partial cutaway of one of a plurality of joints as structured in an embodiment of the present invention.

Accordingly, the dynamic foot plate assembly 1 comprises a base element generally indicated as 20 movably interconnected to at least one side element 10 by at least one joint generally indicated as 30. In FIGS. 11 and 13, a possible alternate embodiment of a joint is represented as 30' and described in greater detail hereinafter. With reference to FIG. 6, additionally, the foot plate assembly 1 further comprises at least one but preferably a plurality of strut members, generally indicated as 60, disposed in interconnecting relation, depending on their position between a support member, generally indicated as 50, and at least one side element generally indicated as 10 or base element 20. With primary reference to FIG. 1, the base element 20 defining at least a portion of the dynamic foot plate assembly 1 in the preferred embodiment includes a curvilinear or other appropriate configuration which at least partially surrounds a rear portion or generally the heel area of the ankle area 100. More specifically, the configuration of the base element 20 may be more specifically defined by an arcuate or semi-circular shape, but any suitable shape will suffice, which accomplishes the intended positioning of the base 20 relative to the ankle area 100. As such, the base element 20 terminates in oppositely disposed free ends 22. Further, a plurality of apertures 21 or other appropriate structure are positioned substantially along the length of the base element 20, and at least one side element 10 and the support member 50. The apertures 21 are disposed and structured to facilitate interconnection of the one or more fixation support struts 60 preferably using appropriate bolts or other connectors 61, described in detail hereinafter with reference to at least FIG. 8. The fixation struts 60 and interconnecting bolts 61 are used to support and variably position the base element 20 and the one or more side elements 10 in a preferred and/or intended stabilized orientation relative to the support member 50 and ankle area 100, so as best to accomplish treatment of the ankle area 100.

Similar type or other appropriately structured connecting members and or supplementary struts 90 may be used to connect a halo-type ring 92 located above the support member 50 and ankle area 100 along the length of the leg and in surrounding relations to the bones of the leg. Such anchoring of the halo ring 92 provides stabilizing support to the support member 50, base element 20 and one or more side elements 10 by virtue of the interconnection between the halo ring 92 and the support member 50 by the plurality of supplementary strut members 90.

Figure 1:
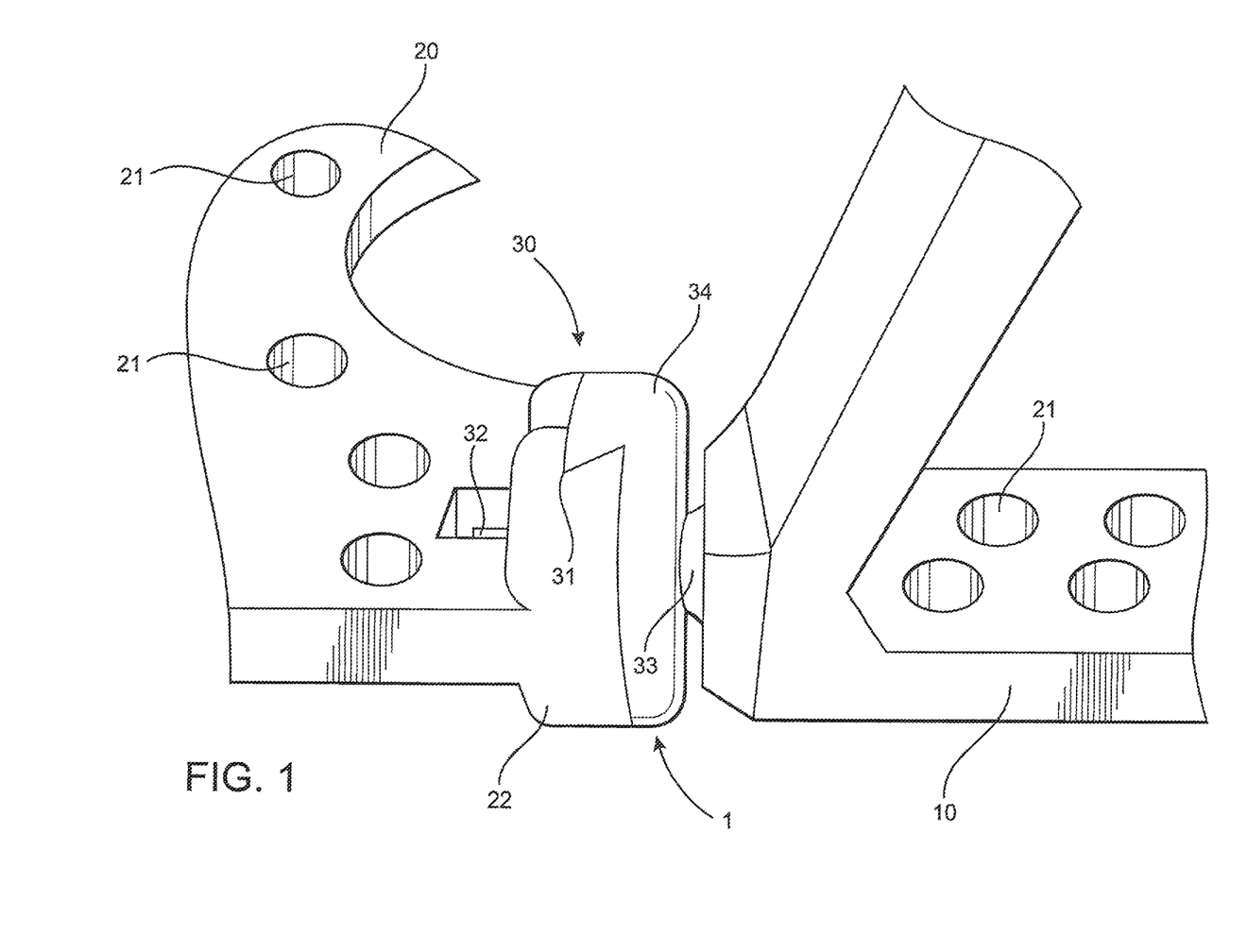
FIG. 1 is a side view in partial cutaway of the preferred embodiment of the present invention.
Figure 2:
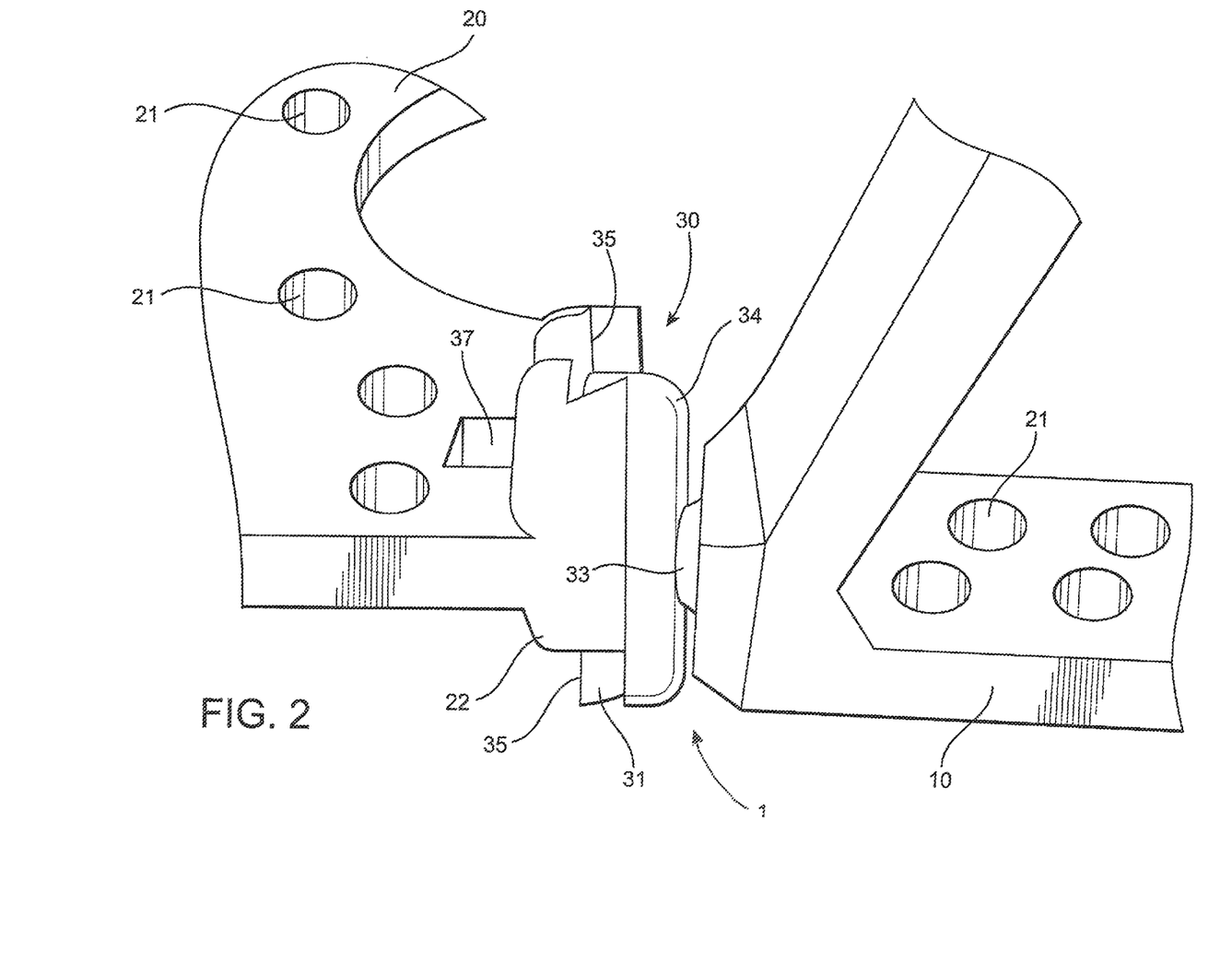
FIG. 2 is a side view in partial cutaway of the joint of the preferred embodiment of FIG. 1.
Figure 3:
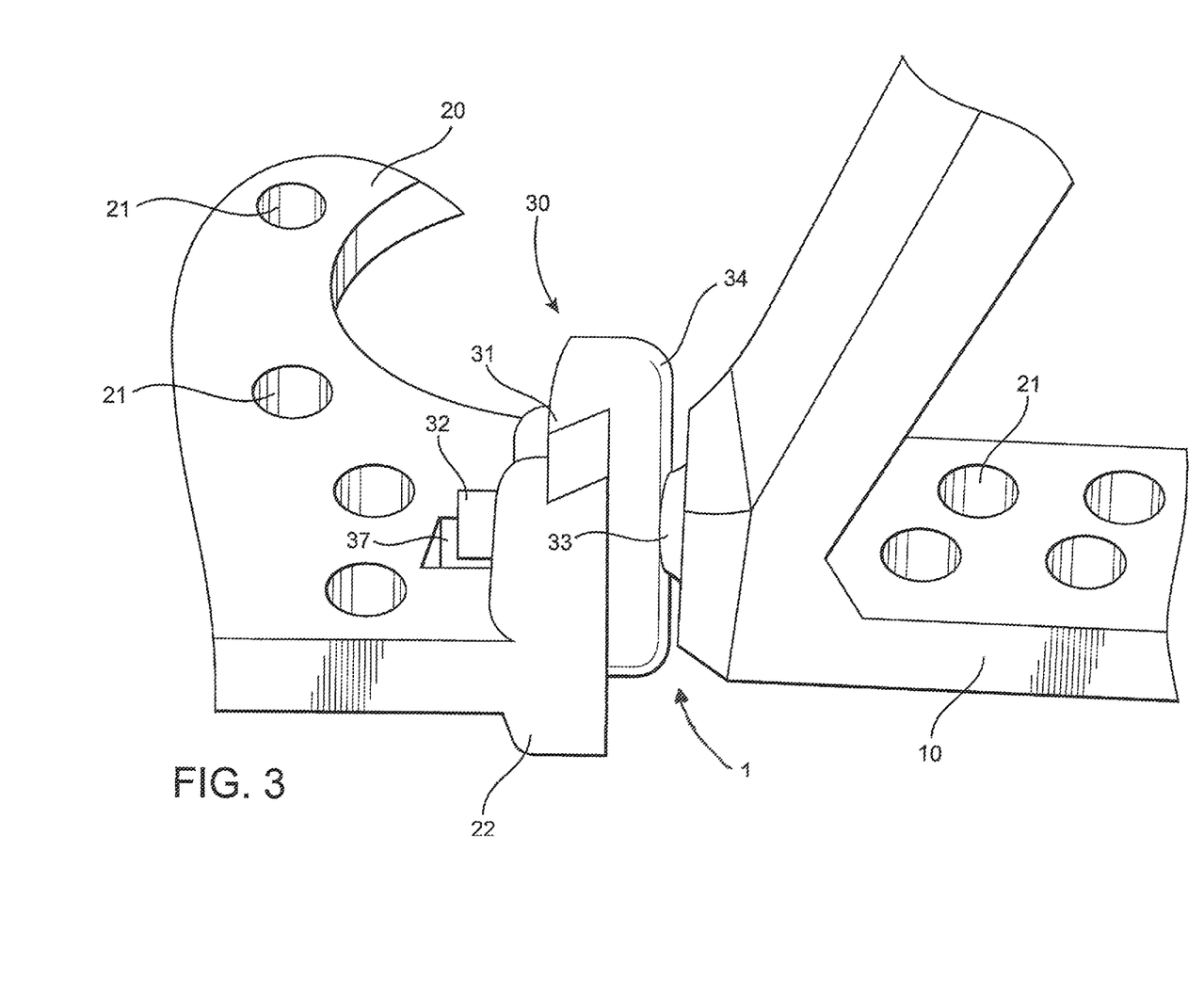
FIG. 3 is a side view in partial cutaway of the joint of the preferred embodiment of FIG. 1.

With primary reference to FIG. 1, the joint 30 as depicted in the preferred embodiment comprises a joint housing 34, an extension element 32, and a pivot element 33. The joint housing 34 can be made of any sufficiently rigid or sturdy material. Also, as represented in FIGS. 1-5, the joint housing 34 is apertured to receive the extension element 32, which extends substantially into and, in this case, through the joint housing 34. In other embodiments, the extension element 32 may only partially recess into the joint housing. The joint housing 34 is cooperatively structured with the distal, free end 22 of the base element 20 to facilitate a variable movement relative to one another. More specifically the joint housing 34 includes a set of flanges 31 extending linearly in a direction substantially perpendicular or transverse to the axis of the joint housing 34 and to the extension element 32. The flanges 31 facilitate a confronting engagement with the adjoining cooperatively configured structure of the free end 22 of the base element 20. The flanges 31 maintain interconnection between the joint housing 34 and the correspondingly disposed free end 22 of the base element 20 while simultaneously facilitating relative linear movement in opposite directions therebetween. Such relative linear movement may be interpreted as relative sliding movement in of the flanges 31 in opposite directions and substantially transverse to the plane of the base 20 as depicted in greater detail in FIGS. 2-5. This sliding, or substantially transverse and/or vertical displacement relative to the base element 20, confers a significant benefit to a medical professional using the dynamic foot plate assembly 1 by allowing the adjustment between the base element 20 and a corresponding one of a possible plurality of side elements 10 into a desired orientation. Such adjustment comprises the varying of the disposition of the base element 20 relative to at least one side element 10 both prior to the onset of and during treatment of the dynamic foot plate 1 relative to the ankle area 100. The present invention also contemplates an alternative embodiment, wherein a side element 10 is properly configured for similar direct confronting engagement of the flanges 31.

The extension element 32 of the joint 30 may be a longitudinal member that extends wholly or substantially through the aperture of the joint housing 34. The extension element 32 is coaxially aligned with the aperture in the joint housing 34 and in transverse relation to length or height of the housing 34 and flanges 31. The extension element 32 may resemble a screw, bolt or other threaded rod-like structure capable of extension through or partially through the aperture of the joint housing 34. The extension element 32 in the preferred embodiment is a threaded elongated member, with the threads extending substantially along the at least a portion of the length of the outer surface of the extension element 32. The extension element 32 is disposed and structured to facilitate a frictional, movable, mating and confronting engagement with opposing threads lining the interior of the central aperture of the joint housing 34. The structure of the extension element 32 allows for the variable adjustment of the disposition or displacement of the base element 20 and a corresponding one of the possible to side elements 10 towards and away from one another. Such variable relative displacement or disposition is achieved by rotation of the extension element 32 about its axis, which can either outwardly extend or inwardly retract the joint housing 34 relative to the corresponding end of the side element 10, via the utilization of the threads extending substantially along the length of the extension element 32.

Figure 4:
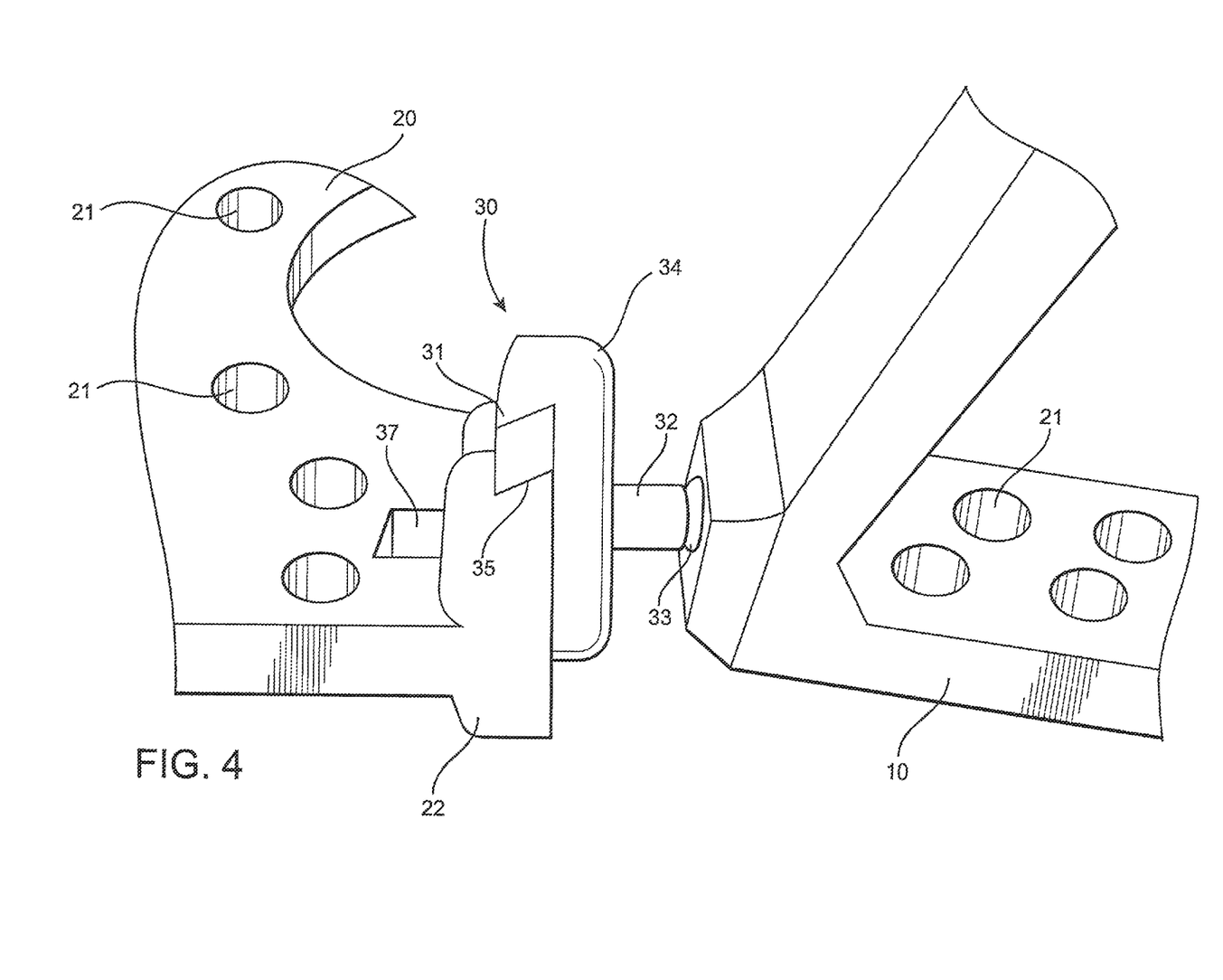
FIG. 4 is a side view in partial cutaway of the joint of the preferred embodiment of FIG. 1.
Figure 5:
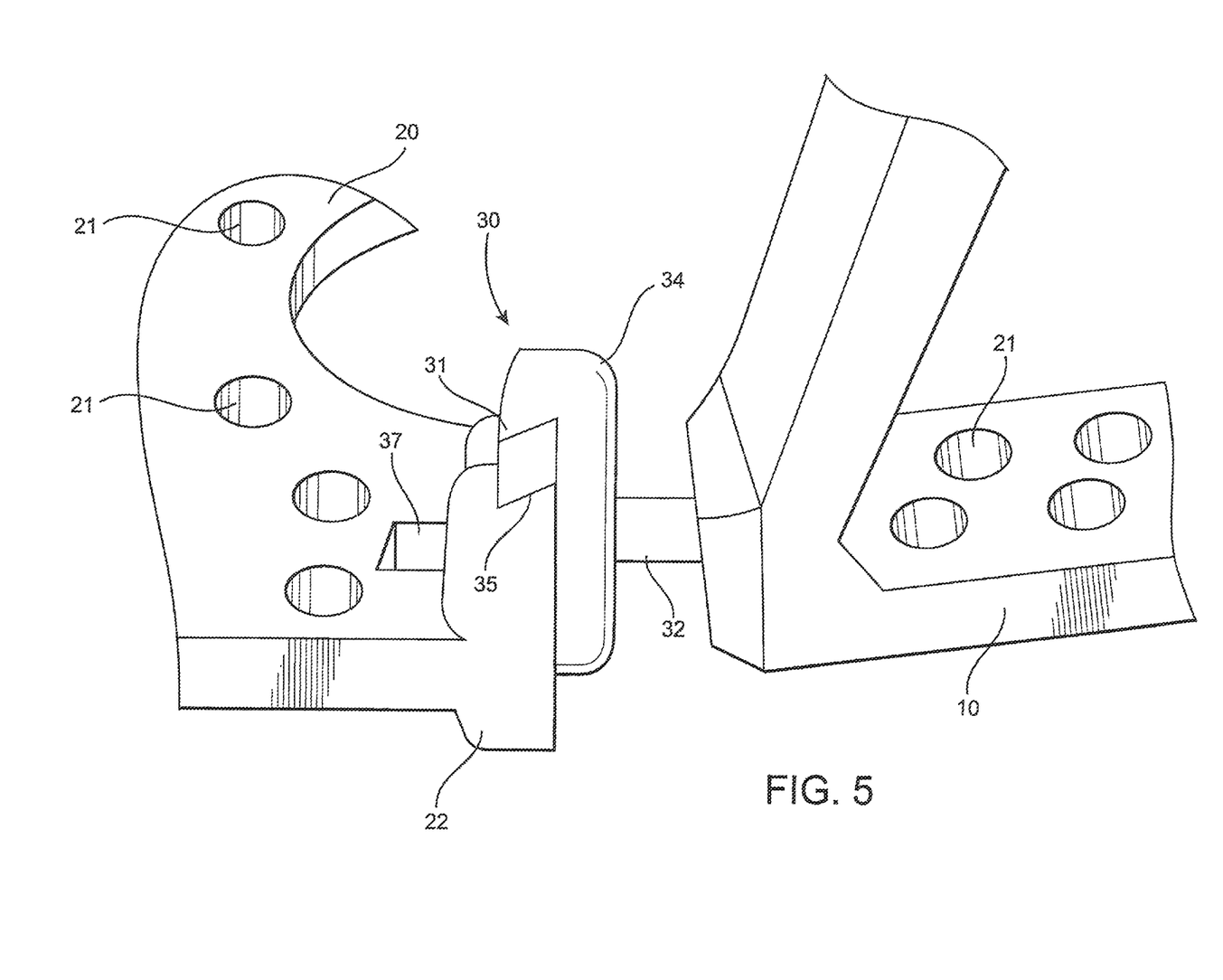
FIG. 5 is a side view in partial cutaway of the joint of the preferred embodiment of FIG. 1.

Attached to the extension element 32 or, alternatively, one end of the extension element 32 itself, is a pivot element 33 structured for an at least partially universal range of motion. The pivot element 33 may substantially resemble a ball disposed in a cooperatively dimensioned and configured socket formed in the corresponding end of the side element 10. The pivot element 33 thereby facilitates the aforementioned at least partially universal movement including a substantially upwardly or downwardly tilting motion as represented by a variance of the angular orientation and or disposition of the longitudinal axis or length of the side element 10 relative to the base element 20 as depicted in FIGS. 4 and 5. Alternatively, in another embodiment, the joint 30 could be configured to connect two side elements 10, allowing for a similar tilting motion by way of the pivot element 33, disposed in a socket in one of the two side elements 10, to vary the angular disposition of the axes between the two side elements 10. The pivot element 33 also facilitates the relative varying of the disposition of a base element 20 and a side element 10, as shown in the preferred embodiment, or between two side elements 10, in a lateral direction, inwardly or outwardly and/or toward or away from the ankle area 101 another. Finally, the joint 30 and the substantially universally movable pivot element 33 may also facilitate a rotational or rotary movement in such a way that does not vary the angular disposition of the base element 20 and side element 10, or as between two side elements 10. More specifically the aforementioned rotational or rotary movement may be defined by an at least partial rotation or angular disposition of the one or more side elements 10 substantially about their own longitudinal axis.

One operative feature of the joint 30 including the pivot element 33 is the versatility thereof which facilitates the above described varied, adjustable movements and/or orientation of the base 20 and one or more side elements 10 relative to one another independently of one another. Such independent, varied relative movements and orientations of the base 20 joint 30 and one or more side elements 10 can be a compound movement that facilitates the at least one of the aforementioned motions, tilting, displacement, lateral or rotary orientation, necessary for a medical professional or other operator to properly dispose a side element 10 and any fixation pens or like structures connected thereto into a predetermined orientation to effect treatment of the ankle area 100.

Another embodiment of the joint is given at 30' as shown in FIG. 13. This embodiment may further comprise a nut 36 or similar centrally apertured structure disposed upon the extension element 32 and coaxially aligned therewith. The nut 36 is capable of translation along the extension element 32 and can be caused to be placed in confronting engagement with the side element 10. This confronting engagement between the nut 36 and the side element 10 restricts or eliminates the movement of the side element 10 facilitated by the pivot element 33 as described above. Additionally, the joint 30' may comprise an alternate embodiment of a joint housing 34' interconnected to a base element 20 or side element 10. This joint housing 34' may comprise a plurality of bolts, nuts, or other compression elements, given as 35. These compression elements 35 may be threaded such that a rotational force, such as with a screwdriver, hex key, wrench, etc. is applied about the central axis, the head of any one of the compression elements 35 exerts a compressive force upon the joint housing 34'. The result of the compressive force is to increase the frictional forces exerted upon the extension element 32, causing the extension element 32 to become frictionally locked in a desired orientation. Consequently, the joint housing 34' may be structured in such a way that the frictional force component of the frictional confronting engagement, as previously described, exerted upon the extension element 32 by the joint housing 34' is capable of being varied. One possible way of doing that is by the inclusion of a gap 37 or similar spacing between two separate parts 37', 37" of the joint housing 34', in which the extension element 32 is disposed. As such, a compressive force exerted by a compression element 35, through e.g. a rotation of the compression element 35 as described above, causes the gap 37 to decrease in width, resulting in the substantially fixed "clamping" of the extension element 32 there between. Consequently, the two parts 37', 37" of the joint housing 34' are forced together, and in turn increase the compression and thus frictional forces, i.e. clamping forces, exerted upon the extension element 32. Thus, the extension element 32 is sandwiched between the two parts 37', 37", causing the extension element 32 to become frictionally locked or clamped in a desired orientation. Rotating the compression element or elements 35 in the opposite direction causes the gap 37 to widen, decreasing the aforementioned clamping forces and unlocking the compression element 32, restoring its capability for previously described movement.

Figure 7:
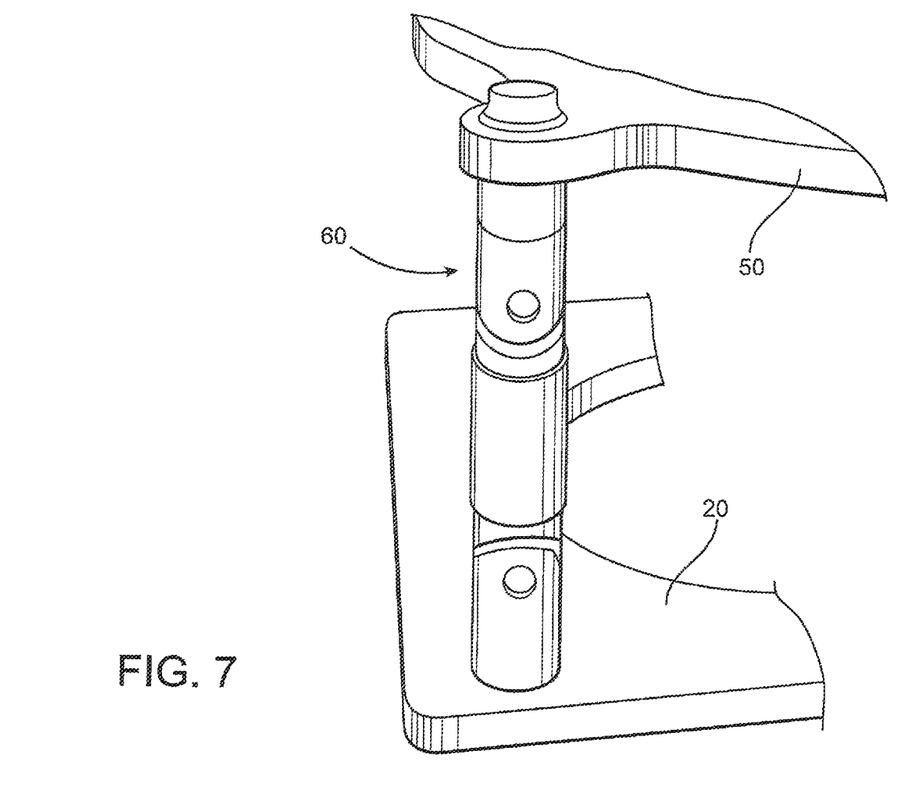
FIG. 7 is a side view in partial cutaway of one of a plurality of strut members as represented in the preferred embodiment of FIG. 1.

Additionally, disposed above the base element 20 and at least partially surrounding the ankle is the aforementioned support member 50, represented in at least FIGS. 6 and 7. With primary reference to FIG. 6, the support member 50 has substantially along its length a plurality of apertures 21 for the connection of fixation struts 60 and possibly fixation pins, (not represented for purposes of clarity). The support member 50 is preferably annular or at least curvilinear, with a configuration in the form of a circle, ellipse, or any other appropriate shape that facilitates its disposition in at least partially surrounding relation to the ankle area 100 as represented throughout the Figures. The act least one or more strut apertures 21 are present on the support member 50 and extend partway or totally through the support member 50 and allows for attachment of the one or more strut members 60 in interconnecting relation between the support member 50 and the base 20 and one or more side elements 10. The method of attachment of the preferred embodiment and alternatives will be discussed in detail below.

Figure 8:
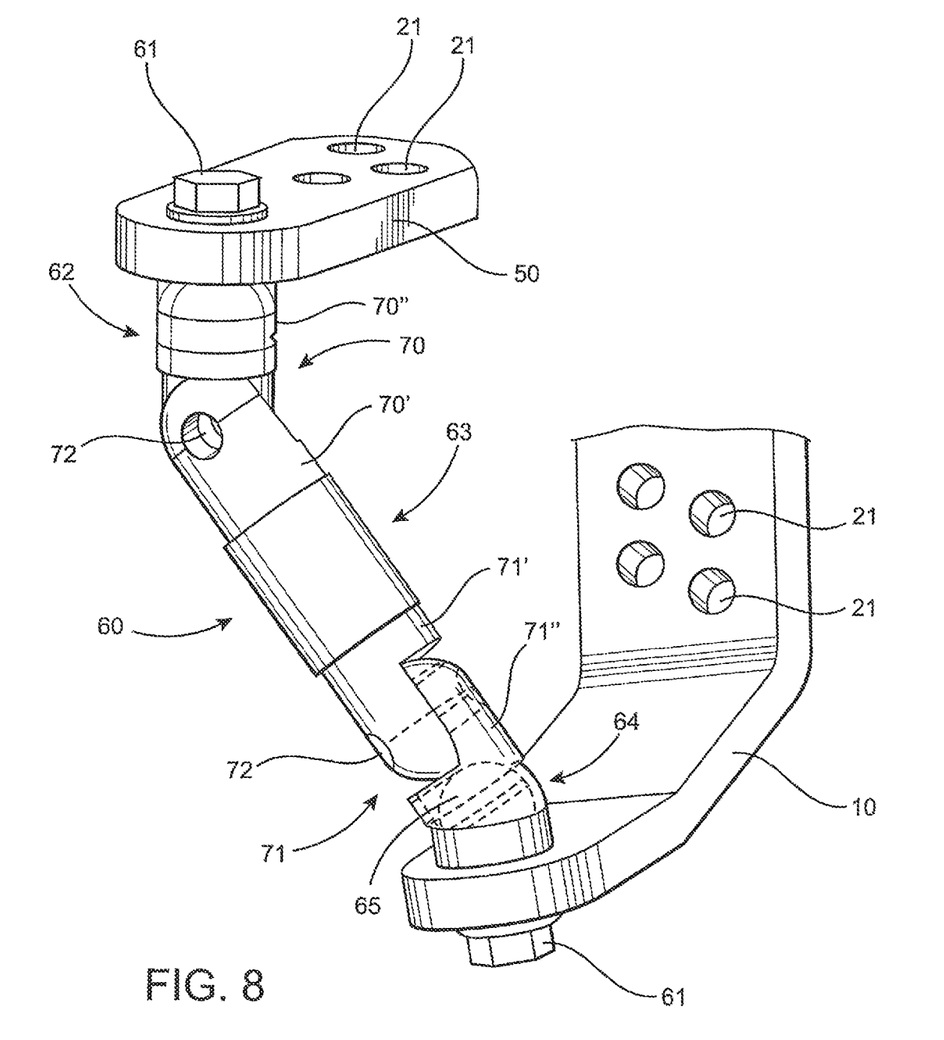
FIG. 8 is a front view in partial cutaway of one of a plurality of strut members, including a representation of the internal structure of corresponding ones of the strut members.

With primary reference to FIG. 8, in at least one embodiment, the one or more strut members 60 comprise a pair of strut attachment elements 61 that attach one end of the strut member 60 to a support member 50 and the opposing end to the side element 10 or, as shown in FIG. 7, a base element 20. With reference to FIGS. 9, 10, and 11, possible alternate embodiments of strut members are given at 60' and 60", to be described in greater detail hereinafter. Returning to FIG. 8, the strut attachment element 61 can be any means of fixed attachment that allows for confronting engagement between the correspondingly disposed ends of the strut member 60 and the aforementioned side element 10, base element 20, or support member 50. As such, the attachment element 61 may comprise a threaded bolt or even a suitably strong adhesive substance. As depicted in the preferred embodiment, the strut attachment element 61 is comprised of a nut that fastens a threaded bolt that passes through an aperture in the intended base element 20, side element 10 and support member 50 to ensure a stable connection or abutment therebetween. The strut member 60 is structured so as to facilitate the variable disposition of the support member 50, a base element 20, and/or a side element 10 relative to the ankle and one another. The strut attachment element 61 that passes through the support member 50 is attached to a first housing 62 and abuts the support member 50. The first housing 62 can be socketed or otherwise structured to receive one end of a first hinge 70, the structure of which will be discussed in detail below. On the opposite end of the first hinge 70 is a second housing 63. The second housing 63 is socketed at either end, or apertured and/or otherwise structured to receive one end of the first hinge 70 and one end of the second hinge 71 as depicted in FIG. 8. The end of the second hinge 71 is disposed within a third housing 64, which abuts and/or is connected to either a base element 20 or a side element 10 in a confronting engagement facilitated by the second of two strut attachment elements 61.

The first hinge 70 is comprised of a primary first hinge member 70', a secondary first hinge member 70", and a hinge fastener 72. The secondary first hinge member 70" is disposed with a hollow, socket or other similar recess in the first housing 62 in such a way as to facilitate the rotary or pivotal motion of the secondary first hinge member 70" relative to the primary first hinge member 70' about the its central axis of fastener 72. The exposed end of the secondary first hinge member 70" is apertured to receive the hinge fastener 72. The secondary first hinge member 70" is movably connected to the primary first hinge member 70', which is similarly apertured as shown in FIG. 8 to receive the cooperatively disposed hinge fastener 72. The primary and secondary first hinge members 70' and 70" by virtue of their rotationally connected abutting ends corresponding to the second housing 63 are cooperatively structured and configured to pivot about a common axis.

Accordingly, one of a pair of hinge fasteners 72 joins the primary first hinge member 70' and the secondary first hinge member 70" and facilitates their rotational or pivotal movement about an axis defined by the central axis of the hinge fastener 72. The hinge fastener 72 can be a bolt and nut or any similar fastening structural composition that allows for tightening to adjust the confrontation between the primary first hinge member 70' and secondary first hinge member 70". By adjusting the confrontation, it is possible to cause the first hinge 70 to become frictionally, but removably locked relative to one another, which is desirable when disposing the dynamic foot plate array 1 into a predetermined position and/or orientation for treatment ankle area 100. When the first hinge 70 is frictionally locked, reducing the tensile forces directed along the central axis of the hinge fastener 72 or "loosening" the hinge fastener 72 will restore the ability for the primary first hinge member 70' and secondary first hinge member 70" to rotate or pivot about the aforementioned axis of the hinge fastener 72. The primary second hinge member 71' and the secondary second hinge member 72" are similarly attached with the second of a pair of hinge fasteners 72, the function of which is substantially the same as set forth above.

Furthermore, the second housing 63, which may be socketed on each end or else centrally apertured, is structured to receive one end the primary first hinge member 70' and in the other end the primary second hinge member 71', as shown in FIG. 8. The second housing 63 is structured to movably interconnect the primary first and second hinge members 70' and 71'. The second housing 63 is further structured to facilitate the rotational movement of the primary members 70' and 71' about an axis, defined as the central axis of the second housing 63.

The second hinge 71 comprises the primary second hinge member 71' and a secondary second hinge member 71" cooperatively structured and configured to pivot about a common axis, defined as the central axis of the aforementioned corresponding hinge fastener 72 that joins the two members 71' and 71".

A third housing 64 is pivotally interconnected to the secondary second hinge member 71" and is structured to facilitate an at least partially universal range of motion of the secondary second hinge member 71", and may substantially resemble of that of a ball 65 in socket 65'.

Figure 12:
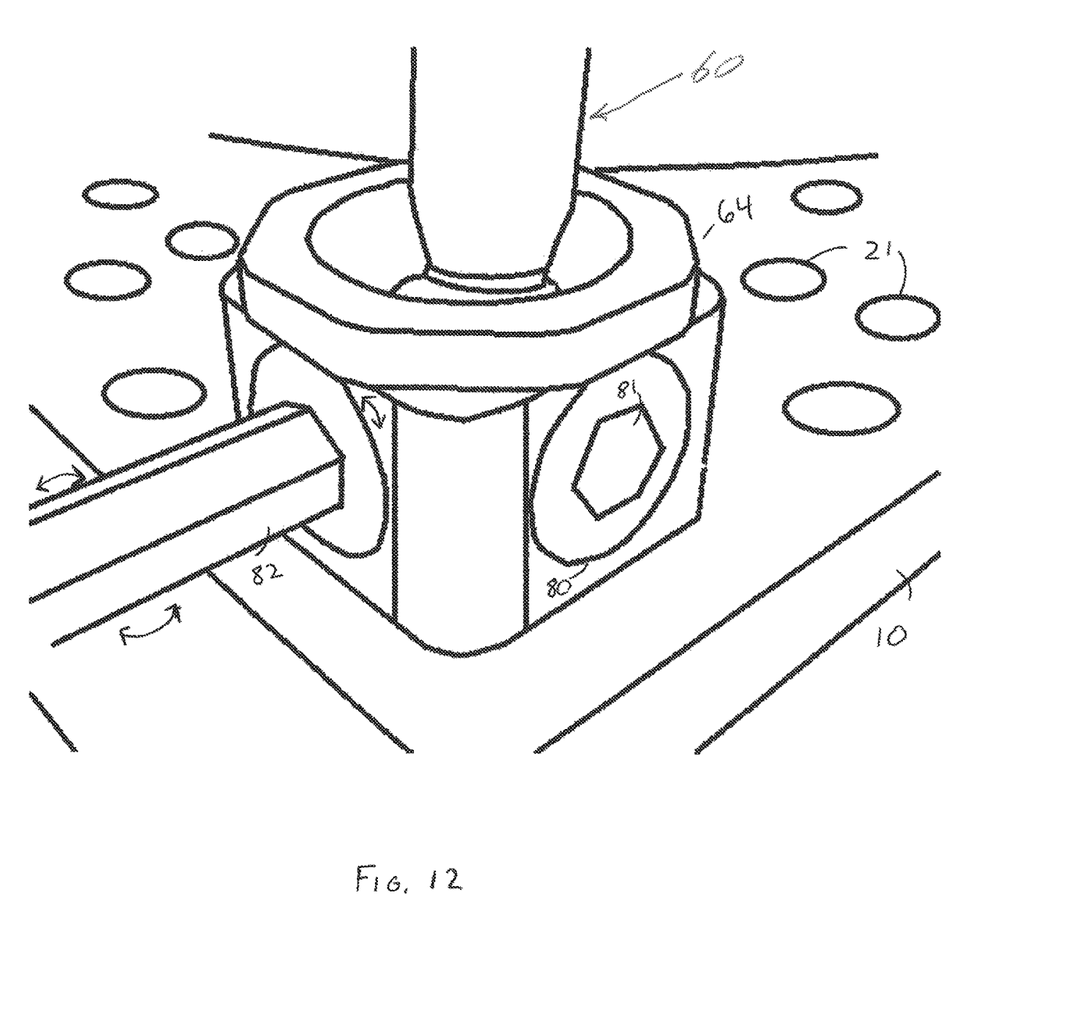
FIG. 12 is a view in partial cutaway of one of a plurality of strut members as structured in another embodiment of the present invention.

Another embodiment of the present invention is shown in FIG. 12 and features a locking mechanism providing for the disposition of the strut member 60 into fixed orientation. The third housing 64 comprises at least one, but may comprise a plurality of, apertures structured to receive a locking bolt 80. The locking bolt 80 is coaxially aligned with the aperture of the third housing 64. The aperture in the third housing 64 is in abutting confrontation with the locking bolt 80, and such abutting confrontation is further defined by the complementary threading of the confronting surfaces of the locking bolt 80 and the third housing 64 as is common of a bolt and a nut. As a result, a rotary force upon the locking bolt 80 about its central axis, which as discussed above is aligned with the central axis of the respective aperture of the third housing 64 into which the locking bolt 80 is inserted, causes the locking bolt 80 to translate along the central axis. Consequently, a rotary force, when applied to the locking bolt 80, can be made to cause the locking bolt 80 to press against the ball of the aforementioned ball in socket assembly, and thereby apply a frictional force sufficient to cause the ball to become frictionally locked and thus unable to move within the socket. The locking bolt 80 may itself be apertured, the aperture 81 being structured to receive a "tool" 82, defined as a tension member structured to provide the rotary force above described. In other embodiments, the locking bolt 80 may be structured to accommodate alternative types of tools 82, such as a Phillips screwdriver, flathead screwdriver, hex key, socket wrench, etc., to facilitate the rotary operation of the locking bolt 80. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A dynamic footplate assembly structured for therapeutic use adjacent the ankle area of the body, said footplate assembly comprising:
    a base element structured to be disposed adjacent a posterior portion of the ankle area,
    at least one side element structured to be disposed adjacent to and extending along a length of a foot of the ankle area,
    at least one joint movably and adjustably interconnecting said base element and said at least one side element, said at least one joint comprising a housing, an extension member and a pivot structure,
    said at least one joint disposed and structured to define variable positioning of said at least one side element into different operative orientations relative to said base element,
    said variable positioning comprising a transverse movement of said housing, in opposite directions, relative to a free end of said base element,
    said transverse movement of said housing defining said different operative orientations to include a variable height spacing between said base element and said at least one side element,
    said variable positioning further comprising a rotational movement of said extension member relative to said housing,
    said rotational movement of said extension member defining different operative orientations to include a variable spacing between said at least one side element and said free end of said base element, and
    a support member structured to be disposed in at least partially surrounding relation to the ankle area, a plurality of strut members collectively interconnecting said support member in spaced relation to and above said base element and said at least one side element.

2. The dynamic footplate assembly as recited in claim 1 wherein said variable positioning further comprises a universal movement of said at least one side element relative to said extension member.

3. The dynamic footplate assembly as recited in claim 2 wherein said universal movement defines said different operative orientations to include a variable angular disposition of said at least one side element relative to said base element.

4. The dynamic footplate assembly as recited in claim 3 wherein said variable angular disposition comprises a variable, laterally angular displacement of said at least one side element, relative to said base element.

5. The dynamic footplate assembly as recited in claim 4 wherein said variable angular disposition comprises a variable rotational angular displacement of said at least one side element about a longitudinal axis of said at least one side element.

6. The dynamic footplate assembly as recited in claim 3 wherein said variable angular disposition comprises a variable rotational angular displacement of said at least one side element about a longitudinal axis of said at least one side element.

7. The dynamic footplate assembly as recited in claim 3 wherein said pivot structure comprises a ball and socket formed on said extension member and said at least one side element.

8. The dynamic footplate assembly as recited in claim 2 wherein said pivot structure is formed on both said extension member and said at least one side element.

9. The dynamic footplate assembly as recited in claim 1 wherein said housing is movably connected in sliding engagement with said free end of said base element.

10. The dynamic footplate assembly as recited in claim 1 wherein said extension member is rotationally connected to both said housing and said at least one side element and concurrently rotational relative thereto.

11. The dynamic footplate assembly as recited in claim 10 wherein said extension member is threadedly connected to said housing.

12. The dynamic footplate assembly as recited in claim 1 wherein at least one strut member of said plurality of strut members is disposed and structured to define a variable angular orientation of said one side element relative to both said base element and said support member.

13. The dynamic footplate assembly as recited in claim 12 wherein said one strut member is pivotally connected concurrently to said one side element and said support member.

14. The dynamic footplate assembly as recited in claim 13 wherein said one strut member is rotationally connected to said one side element and said support member.

15. The dynamic footplate assembly as recited in claim 12 wherein said one strut member comprises a first hinge member, said first hinge member comprising a primary first hinge member and a secondary first hinge member, said primary first hinge member pivotally interconnected to said secondary first hinge member, said first hinge member rotationally interconnected to said support member.

16. The dynamic footplate assembly as recited in claim 15 wherein said one strut member further comprises a strut housing and a second hinge member, said housing rotationally interconnecting said second hinge member to said first hinge member, said second hinge member comprising a primary second hinge member and a secondary second hinge member, said primary second hinge member pivotally interconnected to said secondary second hinge member.

17. The dynamic footplate assembly as recited in claim 12 wherein said one strut member is structured to selectively dispose said base element and said support member into fixed relation with one another.

18. The dynamic footplate assembly as recited in claim 1 wherein said at least one joint is structured for selective disposition into a locked orientation, said locked orientation determinative of said base element and said one side element disposed into a removable, fixed relation with one another.

19. A dynamic footplate assembly structured for therapeutic use adjacent the ankle area of the body, said footplate assembly comprising:
- a base element;
- two side elements;
- two joints each disposed in an interconnecting relation between said base element and a different corresponding one of said two side elements, each of said two joints comprising a housing, an extension member and a pivot structure;
- each of said two joints movably and adjustably interconnecting said base element to a different one of said two side elements;
- each of said two joints disposed and structured to define a variable positioning of a correspondingly disposed one of said two side elements into different operative orientations relative to said base element,
- said variable positioning of each of said two side elements comprising a transverse movement of said housing of a corresponding one of said two joints, in opposite directions, relative to a correspondingly positioned free end of said base element,
- said transverse movement of each of said housings defining said different operative orientations to include a variable height spacing between said base element and each of said two side elements,
- said variable positioning further comprising a rotational movement of said extension member relative to said housing of either of said two joints,
- said rotational movement of said extension member of either of said joints defining different operative orientations to include a variable spacing between a corresponding one of said two side elements and a corresponding free end of said base element, and
- a support member structured to be disposed in at least partially surrounding relation to the ankle area, a plurality of strut members collectively interconnecting said support member in spaced relation to and above said base element and at least one of said two side elements.

20. The dynamic footplate assembly as recited in claim 19 wherein said variable positioning further comprises a universal movement of corresponding ones of said two side members relative to a corresponding one of said extension members.

21. The dynamic footplate assembly as recited in claim 20 wherein said universal movement defines said different operative orientations to include a variable angular disposition of each of said two side elements relative to said base element.

22. The dynamic footplate assembly as recited in claim 21 wherein said variable angular disposition comprises a variable, laterally angular displacement of each of said two side elements relative to said base element.

23. The dynamic footplate assembly as recited in claim 22 wherein said variable angular disposition comprises a variable rotational angular displacement of each of said two side elements about a corresponding longitudinal axis of said two side elements.

* * * * *